(12) United States Patent
Mehta et al.

(10) Patent No.: US 7,592,359 B2
(45) Date of Patent: Sep. 22, 2009

(54) SUBSTITUTED AZABICYCLO HEXANE DERIVATIVES AS MUSCARINIC RECEPTOR ANTAGONISTS

(75) Inventors: Anita Mehta, Plainfield, IL (US); Arundutt Viswanatham Silamkoti, Secunderabad (IN); Jang Bahadur Gupta, Dusseldorf (DE)

(73) Assignee: Ranbaxy Laboratories Limited, Gurgaon (IN)

( * ) Notice: Subject to any disclaimer, the term of this patent is extended or adjusted under 35 U.S.C. 154(b) by 70 days.

(21) Appl. No.: 10/552,617

(22) PCT Filed: Apr. 10, 2003

(86) PCT No.: PCT/IB03/01333

§ 371 (c)(1),
(2), (4) Date: Mar. 16, 2007

(87) PCT Pub. No.: WO2004/089363

PCT Pub. Date: Oct. 21, 2004

(65) Prior Publication Data

US 2007/0287732 A1    Dec. 13, 2007

(51) Int. Cl.
  A61K 31/445    (2006.01)
  A61P 11/00    (2006.01)
  A61P 13/00    (2006.01)
  C07D 211/22    (2006.01)
(52) U.S. Cl. ........................ 514/317; 514/321; 514/329; 514/412; 546/197; 546/224; 546/238
(58) Field of Classification Search .................. 514/323, 514/214.01; 540/584; 546/112
See application file for complete search history.

(56) References Cited

U.S. PATENT DOCUMENTS

| | | | | |
|---|---|---|---|---|
| 3,176,019 | A | 3/1965 | Campbell et al. | 260/293.4 |
| 5,281,601 | A | 1/1994 | Cross et al. | 514/320 |
| 5,948,792 | A | 9/1999 | Tsuchiya et al. | 514/317 |
| 6,130,232 | A | 10/2000 | Mase et al. | 514/318 |
| 6,174,900 | B1 | 1/2001 | Okada et al. | 514/317 |
| 6,307,060 | B1 | 10/2001 | Noe et al. | 548/551 |
| 7,232,835 | B2 * | 6/2007 | Mehta et al. | 514/323 |

FOREIGN PATENT DOCUMENTS

| | | |
|---|---|---|
| EP | 0 325 571 | 7/1989 |
| EP | 0 388 054 | 9/1990 |
| EP | 0 413 455 | 2/1991 |
| EP | 0 801 067 | 10/1997 |
| EP | 0 863 141 | 9/1998 |
| GB | 940540 | 10/1963 |
| JP | 92921/1994 | 4/1994 |
| JP | 135958/1994 | 5/1994 |
| WO | WO 91/09013 | 6/1991 |
| WO | WO 93/16018 | 8/1993 |
| WO | WO 93/16048 | 8/1993 |
| WO | WO 96/33973 | 10/1996 |
| WO | WO 97/45414 | 12/1997 |
| WO | WO 98/05641 | 2/1998 |
| WO | WO 98/29402 | 7/1998 |

OTHER PUBLICATIONS

Vippagunta et al., "Crystalline Solids", Advanced Drug Delivery Reviews, vol. 48, pp. 3-26 (2001).*
Gavezzotti, "Are Crystal Structures Predictable?", Accounts of Chemical Research, vol. 27, pp. 309-314 (1994).*
Morissette et al., Advanced Drug Delivery Reviews, vol. 56, pp. 275-300 (2004).*
Kubo et al., "Cloning, sequencing and expression of complementary DNA encoding the muscarinic acetylcholine receptor", Nature, 323(2):411-416 (1986).
Bonner et al., "Identification of a Family of Muscarinic Acetylcholine Receptor Genes", Science, 237:527-531 (1987).
Eglen et al., "Muscarinic receptor ligands and their theraputic potential", Current Opinion in Chemical Biology, 3:426-432 (1999).
Eglen et al., "Theraputic opportunities from muscarinic receptor research", Trends in Pharmacological Sciences, 22(8):409-414 (2001).
Felder et al., "Theraputic Opportunities for Muscarinic Receptors in the Central Nervous System", Journal of Medicinal Chemistry, 43(23):4333-4353 (2000).
Broadley and Kelly, "Muscarinic Receptor Agonists and Antagonists", Molecules, 6:142-193 (2001).
Birdsall et al., "Muscarinic receptors: it's a knockout", Trends in Pharmacological Sciences, 22(5):215-219 (2001).
de Groat and Yoshimura, "Pharmacology of the Lower Urinary Tract", Annual Review of Pharmacology and Toxicology, 41:691-721 (2001).
Steers, "The future direction of neuro-urology drug research", Current Opinion in CPNS Investigational Drugs2(3):268-282.
Chapple, "Muscarinic receptor antagonists in the treatment of overactive bladder", Urology, 55(Suppl 5A):33-46 (2000).
Steers, Barrot, Wein, "Voiding dysfunction: diagnosis classification and management", In: Adult and Pediatric Urology, ed. Gillenwater, Grayhack, Howards, Duckett. Mosby, St. Louis, MO; 1220-1325, 3rd edition (1996).

(Continued)

Primary Examiner—Brian-Yong S Kwon
Assistant Examiner—Bong-Sook Baek
(74) Attorney, Agent, or Firm—James J. DeYonker, Esq.

(57) ABSTRACT

This invention generally relates to derivatives of substituted azabicyclo hexanes. The compounds of this invention can function as muscarinic receptor antagonists, and can be used for the treatment of various diseases of the respiratory, urinary and gastrointestinal systems mediated through muscarinic receptors. The invention also relates to a process for the preparation of the compounds of the present invention, pharmaceutical compositions containing the compounds of the present invention and the methods of treating the diseases mediated through muscarinic receptors.

3 Claims, No Drawings

OTHER PUBLICATIONS

Sagara et al., "Cyclohexylmethylpiperidinyltriphenylpropioamide: A Selective Muscarinic M3 Antagonist Discriminating against the Other Receptor Subtypes", *Journal of Medicinal Chemistry*, 45:984-987 (2002).

Shacklett and Smith, "The Preparation of Substituted Benzilic Acids", *Journal of the American Chemical Society*, 75:2654-2657 (1953).

Moriya et al., "Affinity Profiles of Various Muscarinic Antagonists for Cloned Human Muscarinic Acetylcholine Receptor (mAChR) Subtypes and mAChRs in Rat Heart and Submandibular Gland", *Life Sciences*, 64(25):2351-2358 (1999).

Cheng and Prusoff, "Relationship between the inhibition constant ($K1$) and the concentration of inhibitor which causes 50 per cent inhibition (I50) of an enzymatic reaction", *Biochemical Pharmacology*, 22:3099-3108 (1973).

* cited by examiner

SUBSTITUTED AZABICYCLO HEXANE DERIVATIVES AS MUSCARINIC RECEPTOR ANTAGONISTS

FIELD OF THE INVENTION

This invention generally relates to derivatives of substituted azabicyclo hexanes.

The compounds of this invention can function as muscarinic receptor antagonists, and can be used for the treatment of various diseases of the respiratory, urinary and gastrointestinal systems mediated through muscarinic receptors.

The invention also relates to a process for the preparation of the compounds of the present invention, pharmaceutical compositions containing the compounds of the present invention and the methods of treating the diseases mediated through muscarinic receptors.

BACKGROUND OF THE INVENTION

Muscarinic receptors as members of the G Protein Coupled Receptors (GPCRs) are composed of a family of 5 receptor sub-types ($M_1$, $M_2$, $M_3$, $M_4$ and $M_5$) and are activated by the neurotransmitter acetylcholine. These receptors are widely distributed on multiple organs and tissues and are critical to the maintenance of central and peripheral cholinergic neurotransmission. The regional distribution of these receptor sub-types in the brain and other organs has been documented. For example, the $M_1$ subtype is located primarily in neuronal tissues such as cerebral cortex and autonomic ganglia, the $M_2$ subtype is present mainly in the heart where it mediates cholinergically induced bradycardia, and the $M_3$ subtype is located predominantly on smooth muscle and salivary glands (*Nature*, 1986; 323: 411; Science, 1987; 237: 527).

A review in *Current Opinions in Chemical Biology*, 1999; 3: 426, as well as in *Trends in Pharmacological Sciences*, 2001; 22: 409 by Eglen et. al., describe the biological potentials of modulating muscarinic receptor subtypes by ligands in different disease conditions like Alzheimer's disease, pain, urinary disease condition, chronic obstructive pulmonary disease etc.

A review in *J. Med. Chem.*, 2000; 43: 4333 by Christian C. Felder et. al. describes therapeutic opportunities for muscarinic receptors in the central nervous system and elaborates on muscarinic receptor structure and function, pharmacology and their therapeutic uses.

The pharmacological and medical aspects of the muscarinic class of acetylcholine agonists and antagonists are presented in a review in *Molecules*, 2001, 6: 142. N. J. M. Birdsall et. al. in *Trends in Pharmacological Sciences*, 2001; 22: 215 have also summarized the recent developments on the role of different muscarinic receptor subtypes using different muscaranic receptors of knock out mice.

Muscarinic agonists such as muscarine and pilocarpine and antagonists such as atropine have been known for over a century, but little progress has been made in the discovery of receptor subtype-selective compounds making it difficult to assign specific functions to the individual receptors. Although classical muscarinic antagonists such as atropine are potent bronchodilators, their clinical utility is limited due to high incidence of both peripheral and central adverse effects such as tachycardia, blurred vision, dryness of mouth, constipation, dementia, etc. Subsequent development of the quarterly derivatives of atropine such as ipratropium bromide are better tolerated than parenterally administered options but most of them are not ideal anti-cholinergic bronchodilators due to lack of selectivity for muscarinic receptor sub-types. The existing compounds offer limited therapeutic benefit due to their lack of selectivity resulting in dose limiting side-effects such as thirst, nausea, mydriasis and those associated with the heart such as tachycardia mediated by the $M_2$ receptor.

Annual review of *Pharmacolobical Toxicol.* 2001; 41: 691, describes the pharmacology of the lower urinary tract infections. Although anti muscarinic agents such as oxybutynin and tolterodine that act non-selectively on muscarinic receptors have been used for many years to treat bladder hyperactivity, the clinical effectiveness of these agents has been limited due to the side effects such as dry mouth, blurred vision and constipation. Tolterodine is considered to be generally better tolerated than oxybutynin. (W. D. Steers et. al. in *Curr. Opin. Invest. Drugs* 2: 268, C. R. Chapple et. al. in *Urology*, 55: 33), Steers W D, Barrot D M, Wein A J, 1996, Voiding dysfunction: diagnosis classification and management. In "Adult and Pediatric Urology," ed. J Y Gillenwatter, J T Grayhack, S S Howards, J W Duckett, pp 1220-1325, St. Louis, Mo.; Mosby. $3^{rd}$ edition.)

Despite these advances, there remains a need for development of new highly selective muscarinic antagonists which can interact with distinct subtypes, thus avoiding the occurrence of adverse effects.

Compounds having antagonistic activity against muscarinic receptors have been described in Japanese patent application Laid Open Number 92921/1994 and 135958/1994; WO 93/16048; U.S. Pat. No. 3,176,019; GB 940,540; EP 0325 571; WO 98/29402; EP 0801067; EP 0388054; WO 9109013; U.S. Pat. No. 5,281,601. U.S. Pat. Nos. 6,174,900, 6,130,232 and 5,948,792; WO 97/45414 are related to 1,4-disubstituted piperidine derivatives; WO 98/05641 describes fluorinated, 1,4-disubstituted piperidine derivatives; WO 93/16018 and WO96/33973 are other close art references.

A report in *J. Med. Chem.*, 2002; 44:984, describes cyclohexylmethyl piperidinyl triphenylpropioamide derivatives as selective $M_3$ antagonist discriminating against the other receptor subtypes.

SUMMARY OF THE INVENTION

The present invention provides substituted azabicyclo hexanes as muscarinic receptor antagonists and are useful as safe and effective therapeutic or prophylactic agents for the treatment of various diseases of the respiratory, urinary and gastrointestinal systems, and process for synthesis of these compounds.

The invention also provides pharmaceutical compositions containing the compounds, and which may also contain pharmaceutically acceptable carriers, excipients or diluents which are useful for the treatment of various diseases of the respiratory, urinary and gastrointestinal systems.

The invention also includes the enantiomers, diastereomers, N-oxides, polymorphs, pharmaceutically acceptable salts and pharmaceutically acceptable solvates, esters and metabolites of these compounds having the same type of activity.

The invention further includes pharmaceutical compositions comprising the compounds of the present invention, their metabolites, esters, enantiomers, diastereomers, N-oxides, polymorphs, or pharmaceutically acceptable salts or pharmaceutically acceptable solvates, in combination with a pharmaceutically acceptable carrier and optionally included excipients.

Other advantages of the invention will be set forth in the description which follows, and in part will be apparent from the description or may be learnt by the practice of the invention.

In accordance with one aspect of the present invention, there are provided compounds having the structure of Formula I:

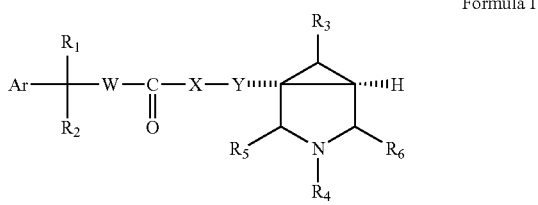

Formula I and their pharmaceutically acceptable salts, pharmaceutically acceptable solvates, esters, enantiomers, diastereomers, N-oxides, polymorphs, or metabolites, wherein Ar represents an aryl or a heteroaryl ring having 1-2 hetero atoms selected from the group consisting of oxygen, sulphur and nitrogen atoms, the aryl or heteroaryl rings may be unsubtituted or substituted by one to three substituents independently selected from lower alkyl ($C_1$-$C_4$), lower perhaloalkyl ($C_1$-$C_4$), cyano, hydroxy, nitro, halogen (e.g. F, Cl, Br, I), lower alkoxy ($C_1$-$C_4$), lower perhaloalkoxy ($C_1$-$C_4$), unsubstituted amino, N-lower alkylamino ($C_1$-$C_4$) or N-lower alkylamino carbonyl ($C_1$-$C_4$);

$R_1$ represents a hydrogen, hydroxy, hydroxymethyl, amino, alkoxy, carbamoyl or halogen (e.g. fluorine, chlorine, bromine and iodine);

$R_2$ represents hydrogen, alkyl, $C_3$-$C_7$ cycloalkyl ring, a $C_3$-$C_7$ cycloalkenyl ring, an aryl or a heteroaryl ring having 1-2 hetero atoms selected from the group consisting of oxygen, sulphur and nitrogen atoms, the aryl or heteroaryl ring may be unsubtituted or substituted by one to three substituents independently selected from lower alkyl ($C_1$-$C_4$), cyano, hydroxy, nitro, lower alkoxycarbonyl, halogen, lower alkoxy ($C_1$-$C_4$), lower perhaloalkoxy ($C_1$-$C_4$), unsubstituted amino, N-lower alkylamino ($C_1$-$C_4$), N-lower alkyl amino carbonyl ($C_1$-$C_4$);

W represents $(CH_2)_p$, where p represents 0 to 1;

X represents an oxygen, sulphur, —NR or no atom, wherein R represents H or alkyl;

Y represents $(CH_2)_q$ wherein q represents 0 to 1;

$R_3$, $R_5$ and $R_6$ are independently selected from H, lower alkyl, COOH, $CONH_2$, $NH_2$, $CH_2NH_2$; and $R_4$ represents hydrogen, $C_1$-$C_{15}$ saturated or unsaturated aliphatic hydrocarbon (straight chain or branched) in which any 1 to 6 hydrogen atoms may be substituted with the group independently selected from halogen, arylalkyl, arylalkenyl, heteroarylalkyl or heteroarylalkenyl, having 1-2 hetero atoms selected from the group consisting of nitrogen, oxygen and sulphur atoms with an option that any 1 to 3 hydrogen atoms on an aryl or heteroaryl ring in said arylalkyl, arylalkenyl, heteroarylalkyl, heteroarylalkenyl group may be substituted with lower alkyl ($C_1$-$C_4$), lower perhaloalkyl ($C_1$-$C_4$), cyano, hydroxy, nitro, lower alkoxycarbonyl, halogen, lower alkoxy ($C_1$-$C_4$), lower perhalo alkoxy ($C_1$-$C_4$), unsubstituted amino, N-lower alkylamino ($C_1$-$C_4$), or N-lower alkylamino carbonyl ($C_1$-$C_4$).

In accordance with a second aspect of the present invention, there is provided a method for treatment or prophylaxis of an animal or a human suffering from a disease or disorder of the respiratory, urinary and gastrointestinal systems, wherein the disease or disorder is mediated through muscarinic receptors.

In accordance with a third aspect of the present invention, there is provided a method for treatment or prophylaxis of an animal or a human suffering from a disease or disorder associated with muscarinic receptors, comprising administering to a patient in need thereof, an effective amount of muscarinic receptor antagonist compound as described above.

In accordance with a fourth aspect of the present invention, there is provided a method for treatment or prophylaxis of an animal or a human suffering from a disease or disorder of the urinary system which induce urinary disorders such as urinary incontinence, lower urinary tract symptoms (LUTS), etc.; respiratory system such as bronchial asthma, chronic obstructive pulmonary disorders (COPD), pulmonary fibrosis, etc.; and gastrointestinal system such as irritable bowel syndrome, obesity, diabetes and gastrointestinal hyperkinesis with compounds as described above, wherein the disease or disorder is associated with muscarinic receptors, comprising administering to a patient in need thereof, an effective amount of compounds as described above.

In accordance with a fifth aspect of the present invention, there is provided a process for preparing the compounds as described above.

The compounds of the present invention exhibit significant potency in terms of their activity, which was determined by in vitro receptor binding and functional assays. Some of the compounds of the present invention were found to be potent muscarinic receptor antagonists with high affinity towards $M_3$ receptors. Therefore, the present invention provides pharmaceutical compositions for treatment of diseases or disorders associated with muscarinic receptors. Compounds and compositions described herein can be administered orally or parenterally.

DETAILED DESCRIPTION OF THE INVENTION

The compounds described herein may be prepared by the techniques well known in the art and familiar to the average synthetic organic chemist. In addition, the compounds described herein may be prepared by the following reaction sequences.

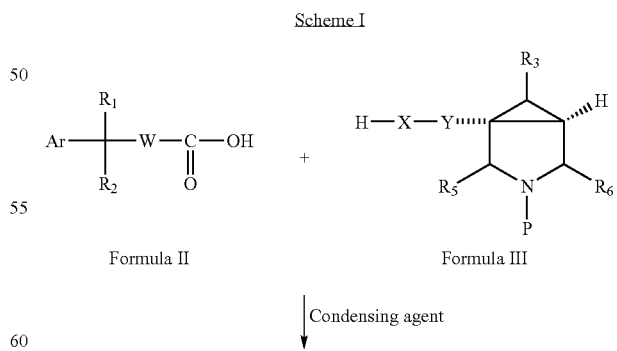

Scheme I

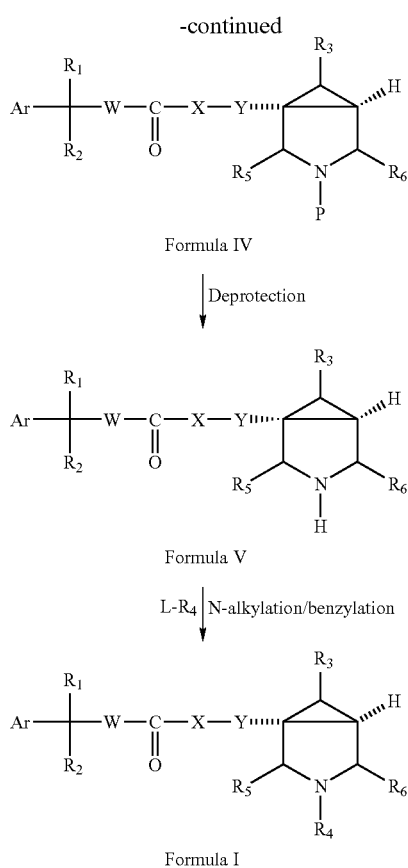

Formula IV

Deprotection

Formula V

L-R$_4$ | N-alkylation/benzylation

Formula I

The compounds of Formula I of the present invention may be prepared by the reaction sequence as shown in Scheme I. The preparation comprises condensing a compound of Formula II with the compound of Formula III wherein Ar represents an aryl or a heteroaryl ring having 1-2 hetero atoms selected from the group consisting of oxygen, sulphur and nitrogen atoms, the aryl or heteroaryl rings may be unsubtituted or substituted by one to three substituents independently selected from lower alkyl ($C_1$-$C_4$), lower perhaloalkyl ($C_1$-$C_4$), cyano, hydroxy, nitro, halogen (e.g. F, Cl, Br, I), lower alkoxy ($C_1$-$C_4$), lower perhaloalkoxy ($C_1$-$C_4$), unsubstituted amino, N-lower alkylamino ($C_1$-$C_4$) or N-lower alkylamino carbonyl ($C_1$-$C_4$);

R$_1$ represents a hydrogen, hydroxy, hydroxymethyl, amino, alkoxy, carbamoyl or halogen (e.g. fluorine, chlorine, bromine and iodine);

R$_2$ represents hydrogen, alkyl, $C_3$-$C_7$ cycloalkyl ring, a $C_3$-$C_7$ cycloalkenyl ring, an aryl or a heteroaryl ring having 1-2 hetero atoms selected from the group consisting of oxygen, sulphur and nitrogen atoms, the aryl or a heteroaryl ring may be unsubstituted or substituted by one to three substituents independently selected from lower alkyl ($C_1$-$C_4$), cyano, hydroxy, nitro, lower alkoxycarbonyl, halogen, lower alkoxy ($C_1$-$C_4$), lower perhaloalkoxy ($C_1$-$C_4$), unsubstituted amino, N-lower alkylamino ($C_1$-$C_4$), N-lower alkyl amino carbonyl ($C_1$-$C_4$);

W represents $(CH_2)_p$, where p represents 0 to 1;

X represents an oxygen, sulphur, —NR or no atom, wherein R represents H or alkyl;

Y represents $(CH_2)_q$ wherein q represents 0 to 1;

R$_3$, R$_5$ and R$_6$ are independently selected from H, lower alkyl, COOH, CONH$_2$, NH$_2$, CH$_2$NH$_2$;

R$_4$ represents hydrogen, $C_1$-$C_{15}$ saturated or unsaturated aliphatic hydrocarbon (straight chain or branched) in which any 1 to 6 hydrogen atoms may be substituted with the group independently selected from halogen, arylalkyl, arylalkenyl, heteroarylalkyl or heteroarylalkenyl, having 1-2 hetero atoms selected from the group consisting of nitrogen, oxygen and sulphur atoms with an option that any 1 to 3 hydrogen atoms on an aryl or heteroaryl ring in said arylalkyl, arylalkenyl, heteroarylalkyl, heteroarylalkenyl group may be substituted with lower alkyl ($C_1$-$C_4$), lower perhaloalkyl ($C_1$-$C_4$), cyano, hydroxy, nitro, lower alkoxycarbonyl, halogen, lower alkoxy ($C_1$-$C_4$), lower perhalo alkoxy ($C_1$-$C_4$), unsubstituted amino, N-lower alkylamino ($C_1$-$C_4$), N-lower alkylamino carbonyl ($C_1$-$C_4$); and P is any group which can be used to protect an amino group, for example, benzyl, t-butyloxy carbonyl in the presence of a condensing agent to give a protected compound of Formula IV, which on deprotection through reaction with a deprotecting agent in an organic solvent gives an unprotected compound of Formula V which is finally N-alkylated or benzylated with a suitable alkylating or benzylating agent L-R$_4$ to give compounds of Formula I wherein L is any leaving group and R$_4$ is as defined above.

The reaction of the compound of Formula II with a compound of Formula III to give compounds of Formula IV can be carried out in the presence of a condensing agent, for example 1-(3-dimethylamino propyl)-3-ethyl carbodiimide hydrochloride (EDC) and 1,8-diazabicyclo[5.4.0]undec-7-ene (DBU).

The reaction of the compound of Formula II with a compound of Formula III to give compounds of Formula IV can be carried out in a suitable solvent, for example N,N-dimethylformamide, dimethylsulfoxide, toluene and xylene at a temperature ranging from about 0° to about 140° C.

The deprotection of the compound of Formula IV to give compounds of Formula V can be carried out with a deprotecting agent, for example palladium on carbon, trifluoroacetic acid (TFA) and hydrochloric acid.

The deprotection of the compound of Formula IV to give compounds of Formula V can be carried out in a suitable organic solvent, for example methanol, ethanol, tetrahydrofuran and acetonitrile at a suitable temperature ranging from about 10° C. to about 50° C.

The N-alkylation or benzylation of the compound of Formula V to give compounds of Formula I can be carried out with a suitable alkylating or benzylating agent, L-R$_4$ wherein L is any leaving group, known in the art, for example halogen, O-mestyl and O-tosyl group.

The N-alkylation or benzylation of the compound of Formula V to give compounds of Formula I can be carried out in a suitable organic solvent such as N,N-dimethylformamide, dimethyl sulfoxide, tetrahydrofuran and acetonitrile, at a suitable temperature ranging from about 25° C. to about 100° C.

In the above scheme, where specific bases, condensing agents, protecting groups, deprotecting agents, N-alkylating/benzylating agents, solvents, catalysts etc. are mentioned, it is to be understood that other bases, condensing agents, protecting groups, deprotecting agents, N-alkylating/benzylating agents, solvents, catalysts etc. known to those skilled in the art may be used. Similarly, the reaction temperature and duration may be adjusted according to the desired needs.

Suitable salts of compound represented by the Formula I were prepared so as to solubilise the compound in aqueous medium for biological evaluations. Examples of such salts are pharmacologically acceptable salts such as inorganic acid salts (e.g. hydrochloride, hydrobromide, sulphate, nitrate and phosphate), organic acid salts (e.g. acetate, tartrate, citrate, fumarate, maleate, toluenesulphonate and methanesulphonate). When carboxyl group is included in the Formula I as a substituent, it may be an alkali metal salt (e.g. sodium, potassium, calcium, magnesium and the like). These salts may be prepared by the usual prior art techniques, such as treating the compound with equivalent amount of inorganic or organic acid or base in a suitable solvent.

An illustrative list of particular compounds which are capable of being produced by Scheme I and also shown in Table 1 include:

| Compound No. | Chemical Name |
|---|---|
| 1. | (1α,5α)-[3-benzyl-3-azabicyclo[3.1.0]-hex-1-(methyl)-yl]-2-hydroxy-2,2-diphenylcarboxylic ester. |
| 2. | (1α,5α)-[3-benzyl-3-azabicyclo[3.1.0]-hex-1-(methyl)-yl]-2-hydroxy-2-cyclohexyl-2-phenylcarboxylic ester. |
| 3. | (1α,5α)-[3-benzyl-3-azabicyclo[3.1.0]-hex-1-(methyl)-yl]-2-hydroxy-2-cyclopentyl-2-phenylcarboxylic ester. |
| 4. | (1α,5α)-[3-benzyl-3-azabicyclo[3.1.0]-hex-1-yl]-2-hydroxy-methyl-2-phenylacetamide. |
| 5. | (1α,5α)-[3-benzyl-3-azabicyclo[3.1.0]-hex-1-yl]-2-hydroxy-2,2-diphenylacetamide. |
| 6. | (1α,5α)-[3-(2-methyl-2-pentenyl)-3-azabicyclo[3.1.0]-hex-1-(methyl)-yl]-2-hydroxy-2-cyclohexyl-2-phenylcarboxylic ester. |
| 7. | (1α,5α)-[3-(3,4-methylenedioxyphenyl)ethyl]-3-azabicyclo[3.1.0]-hex-1-(methyl)-yl]-2-hydroxy-2-cyclohexyl-2-phenylcarboxylic ester. |

TABLE 1

Formula I

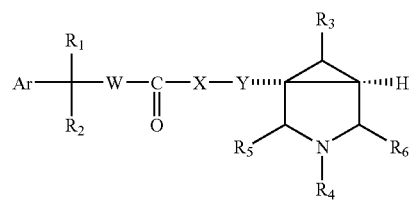

(wherein W = (CH$_2$)p where p = 0, R$_3$ = R$_6$ = R$_5$ = H)

| Compound No. | Ar | X | Y | R$_1$ | R$_2$ | R$_4$ |
|---|---|---|---|---|---|---|
| 1 | phenyl | O | CH$_2$ | OH | 4-methylphenyl | benzyl (phenylethyl) |
| 2 | phenyl | O | CH$_2$ | OH | cyclohexyl | phenylethyl |
| 3 | phenyl | O | CH$_2$ | OH | cyclopentyl | phenylethyl |
| 4 | phenyl | NH | — | CH$_2$OH | H | phenylethyl |
| 5 | phenyl | NH | — | OH | phenyl | phenylethyl |
| 6 | phenyl | O | CH$_2$ | OH | cyclohexyl | 2-methyl-2-pentenyl |
| 7 | phenyl | O | CH$_2$ | OH | cyclohexyl | 2-(3,4-methylenedioxyphenyl)ethyl |

EXPERIMENTAL DETAILS

Various solvents, such as acetone, methanol, pyridine, ether, tetrahydrofuran, hexanes, and dichloromethane were dried using various drying reagents according to the procedures well known in the literature. IR spectra were recorded as nujol mulls or a thin neat film on a Perkin Elmer Paragon instrument, Nuclear Magnetic Resonance (NMR) were recorded on a Varian XL-300 MHz instrument using tetramethylsilane as an internal standard.

Example 1

Preparation of (1α,5α)-[3-benzyl-3-azabicyclo[3.1.0]-hex-1-(methyl)-yl]-2-hydroxy-2,2-diphenylcarboxylic ester (Compound No. 1)

Step-a: Preparation of 3-benzyl-3-azabicyclo[3.1.0]hexane-1-carboxylic acid ethyl ester To a suspension of 3-benzyl-3-azabicyclo[3.1.0]hexane-1-carboxylic acid (8.5 gm, 0.0390 mole), (prepared as described in EP 0413455A2) in ethyl alcohol (250 ml) was added conc. $H_2SO_4$ (10 ml). The resulting pale yellow solution was heated at reflux for 2 hours, cooled to 0° C. and neutralized with aqueous ammonia. The neutralized solution was concentrated and was dissolved in dichloromethane. The organic layer was washed with saturated $NaHCO_3$, water and brine. The organic layer was dried over anhydrous $Na_2SO_4$ and was concentrated to give the crude product which was further purified by column chromatography (100-200 mesh, silicagel), eluting the compound with 5% ethyl acetate in hexane to give the pure product as yellow oil.

IR: 1721.4 cm$^{-1}$ $^1$HNMR (CDCl$_3$): 7.20-7.29 (m, 5H), 4.0 (q, J=7.12, 2H), 3.61 (s, 2H), 3.04 (d, J=8.9 Hz, 1H), 2.92 (d, J=8.8 Hz, 1H), 2.70 (d, J=8.0 Hz, 1H), 2.42 (m, 1H), 1.90 (m, 1H), 1.46 (m, 1H), 1.29 (m, 1H), 1.20-1.28 (t, J=7.1 Hz, 3H)

Step-b: Preparation of 3-benzyl-1-hydroxymethyl-3-azabicyclo[3.1.0]hexane

A solution of 3-benzyl-3-azabicyclo[3.1.0]hexane-1-carboxylic acid ethyl ester (2.5 gm, 0.0108 mole) in tetrahydrofuran (20 ml) was added to a suspension of lithium aluminium hydride (0.966 gm, 0.026 mole) in tetrahydrofuran (50 ml). The resulting mixture was heated to reflux for 2 hours. The reaction mixture was carefully quenched with saturated aqueous NH$_4$Cl (1 ml), treated with ethyl acetate (50 ml) and stirred for 1 hour. The solution was filtered and the removal of solution from the filtrate provided the crude title product which was purified by column chromatography (100-200 mesh, silicagel), eluting the compound with 15% ethyl acetate in hexane to give pure product as a colorless oil.

$^1$HNMR (CDCl$_3$): 7.21-7.31 (brs, 5H), 3.66-3.74 (m, 2H), 3.60 (s, 2H), 3.00 (d, J=8.4 Hz, 1H), 2.92 (d, J=8.4 Hz, 1H)), 2.40 (d, J=8.2 Hz, 2H), 1.22-1.27 (m, 2H), 1.10-1.11 (m, 1H), 0.43-0.47 (m, 1H).

Step-c: Preparation of 3-benzyl-1-methanesulphonyl-3-azabicyclo[3.1.0]hexane To a solution of 3-benzyl-1-hydroxymethyl-3-azabicyclo[3.1.0]hexane in ethyl acetate were added triethylamine (2.15 gm, 0.02125 mole) and methane sulphonylchloride (1.947 gm, 0.017 mole). The mixture was stirred at 0° C. for 1 hour. The reaction was quenched by the addition of saturated NaHCO$_3$. The separated organic layer was washed with water, brine, dried and evaporated to give the crude product, which was used as such for further reaction.

Step-d: Preparation of (1α,5α)-[3-benzyl-3-azabicyclo[3.1.0]-hex-1-(methyl)-yl]-2-hydroxy-2,2-diphenylcarboxylic ester A solution containing diphenylglycolic acid (commercially available) (0.389 gm, 0.0017 mole), 3-benzyl-1-methane sulphonyl-3-azabicyclo[3.1.0]hexane (0.40 gm, 0.0014 mole) and 1,8-diazabicyclo[5.4.0]undec-7-ene (0.323 gm, 0.00213 mole) in toluene (50 ml) was refluxed for 2 hours. The solution was cooled to room temperature. The solution was dried on rotary evaporator. The oil obtained was purified on column chromatography (100-200 mesh, silicagel), eluting the compound with 5% ethyl acetate in hexane to give the pure product as a white solid.

m.p.: 65.2° C.

IR: 1707.4 cm$^{-1}$ $^1$HNMR: 7.19-7.49 (m, 15H), 4.42 (s, 2H), 3.42 (d, J=9 Hz, 2H), 2.77-2.87 (dd, 9 Hz, 2H), 2.22 (m, 1H), 2.10 (d, J=9 Hz, 1H), 1.22-1.26 (m, 1H), 1.11-1.12 (m, 1H), 0.45-0.49 (m, 1H).

Example 2

Preparation of (1α,5α)[3-benzyl-3-azabicyclo[3.1.0]-hex-1-(methyl)-yl]-2-hydroxy-2-cyclohexyl-2-phenylcarboxylic ester (Compound No. 2)

A solution of 2-cyclohexyl-2-hydroxy-2-phenylacetic acid (prepared as described in J. Amer. Chem. Soc., 75, 2654, 1953) (0.398 g, 0.0017 mole), 3-benzyl-1-methane sulphonyl-5-azabicyclo[3.1.0]hexane (0.40 gm, 0.0014 mole) and 1,8-diazabicyclo[5.4.0]undec-7-ene (323 mg, 0.002 mole) was refluxed for 1 hour. The solution was cooled to room temperature and stripped off the solvent to give the crude product, which was further purified on column chromatography (100-200 mesh, silicagel), eluting the compound with 5% ethyl acetate in hexane to give the desired product.

IR: 1721.0 cm$^{-1}$ $^1$HNMR: 7.64-7.68 (m, 2H), 7.26-7.38 (m, 8H), 4.26 (s, 2H), 3.73 (bs, 1H), 3.56-3.73 (m, 2H), 2.90-2.95 (m, 2H), 2.25-2.30 (m, 3H), 1.13-1.4 (m, 12H), 0.25 (m, 1H)

Example 3

Preparation of (1α,5α)-[3-benzyl-3-azabicyclo[3.1.0]hex-1-(methyl)-yl]-2-hydroxy-2-cyclopentyl-2-phenylcarboxylic ester (Compound No. 3)

A solution of 2-cyclopentyl-2-hydroxy-2-phenyl acetic acid (prepared as described in J. Amer. Chem. Soc., 75, 2654, 1953) (375 mg, 0.0017 mole), 3-benzyl-1-methane sulphonyl-3-azabicyclo[3.1.0]hexane (400 mg, 0.00142 mole) and 1,8-diazabicyclo[5.4.0]undec-7-ene (323 mg, 0.00213 mole) in toluene (50 ml) was refluxed for 2 hour. The solution was cooled to room temperature and stripped off the solvent to give crude oily product. The crude product was further purified by column chromatography (100-200 mesh, silicagel), eluting the compound with 5% ethyl acetate in hexane to give the desired product.

IR: 1720.3 cm$^{-1}$ $^1$HNMR (CDCl$_3$): 7.17-7.66 (m, 10H), 4.21 (s, 2H), 3.75 (bs, 1H), 3.53 (s, 2H), 2.86-2.91 (m, 2H), 2.21-2.27 (m, 2H), 1.31-1.38 (m, 8H), 1.12-1.15 (m, 2H), 0.25 (m, 1H).

Example 4

Preparation of (1α,5α)-N-[3-benzyl-3-azabicyclo [3.1.0]hex-1-yl]-2-hydroxymethyl-2-phenylacetamide (Compound No. 4)

To a cooled solution of 3-hydroxy-2-phenylpropionic acid (353 mg, 0.0021 moles, commercially available) and 1-amino-3-benzyl-3-azabicyclo[3.1.0]hexane (400 mg, 0.00212 moles, prepared as described in EP 0413455A2) in DMF (50 ml) was added N-methylmorpholine (536 mg, 0.0053 mole) followed by the addition of hydroxybenzotriazole (286 mg, 0.002 mole) and stirred at 0° C. for one hour. 1-(3-dimethylaminopropyl)-3-ethylcarbodiimide hydrochloride (400 mg, 0.002 mole) was then added. The solution was allowed to attain room temperature and was further stirred for 24 hours. The reaction mixture was quenched with water and extracted with ethyl acetate. The organic layer was washed with saturated NaHCO$_3$, water and brine. The organic layer was dried over anhydrous Na$_2$SO$_4$ and concentrated on rotary evaporator to give the crude product, which was further purified on column chromatography (100-200 mesh, silicagel), eluting the compound with 30% ethyl acetate in hexane to give a yellow oil.

IR: 1657.9 cm$^{-1}$ $^1$HNMR (CDCl$_3$): 7.20-7.52 (m, 10H), 5.9 (s, 1H), 4.07-4.10 (m, 2H), 3.60-3.62 (bs, 2H), 3.02-3.07 (m, 1H), 2.89-2.90 (m, 1H), 2.65-2.86 (m, 1H), 2.49-2.52 (m, 1H), 1.51 (bs, 2H), 1.3-1.5 (bs, 1H), 0.63-0.66 (bs, 1H)

Example 5

Preparation of (1α,5α)-N-[3-benzyl-3-azabicyclo [3.1.0]-hex-1-yl]-2-hydroxy-2,2-diphenylacetamide (Compound No. 5)

To a cooled solution of diphenylglycolic acid (269.5 mg, 0.001 moles) and 1-amino-3-benzyl-3-azabicyclo[3.1.0]hexane (222 mg, 0.0011 mole, prepared as described in EP0413455A2) in DMF (50 ml) was added N-methyl morpholine (298 mg, 0.003 mole), followed by 1-hydroxybenzotriazole (159 mg, 0.0011 mole) and stirred at 0° C. for 1 hour. 1-(3-dimethylaminopropyl)-3-ethylcarbodiimide hydrochloride (225 mg, 0.0011 mol) was then added. The solution was allowed to attain room temperature and stirred for one day. The reaction mixture was quenched with water and extracted with ethyl acetate. The organic layer was washed with saturated NaHCO$_3$, water and brine. The organic layer was dried over anhydrous Na$_2$SO$_4$ and concentrated in vacuo to give the crude product which was further purified by column chromatography (100-200 mesh, silicagel), eluting the compound with 30% ethyl acetate in hexane to give a pale yellow powder.

m.p: 137.5°-138.6° C.

IR (DCM): 1662.6 cm$^{-1}$ $^1$HNMR (CDCl$_3$): 7.24-7.34 (m, 15H), 6.67 (s, 1H), 3.82 (bs, 1H); 3.66 (s, 2H), 3.0 (d, J=8.0 Hz, 1H), 2.87 (d, J=8.4 Hz, 1H), 2.66-2.70 (m, 1H), 2.54 (d, J=8 Hz, 1H), 1.56-1.58 (m, 1H), 1.37-1.40 (m, 1H), 0.67-0.72 (m, 1H)

Example 6

Preparation of (1α,5α)-N-[3-(2-methyl-2-pentenyl)-3-azabicyclo[3.1.0]-hex-1-(methyl)yl]-2-hydroxy-2-cyclohexyl-2-phenylcarboxylic ester (Compound No. 6)

Step-a: Preparation of (1α,5α)-[3-azabicyclo[3.1.0]-hex-1-(methyl)-yl]-2-hydroxy-2-cyclohexyl-2-phenylcarboxylic ester A solution of Compound No. 2 (2.25 g, 0.005 mole) in methanol was taken in parr bottle. To this was added 10% Pd on C (dry). The solution was subjected to hydrogenation in parr hydrogenation apparatus for 4 hours at 60 psi pressure. The reaction mixture was then filtered. The filtrate was concentrated to give the desired product as an off white semi solid mass.

$^1$HNMR (CDCl$_3$): 7.62-7.65 (m, 2H), 7.20-7.36 (m, 3H), 4.25-4.37 (m, 2H), 2.88-3.46 (m, 4H), 2.26 (bs, 1H), 1.18-1.84 (m, 13H), 0.6-0.72 (m, 1H).

IR (DCM): 1661 cm$^{-1}$

Step-b: (1α,5α)-N-[3-(2-methyl-2-pentenyl)-3-azabicyclo[3.1.0]-hex-1-(methyl)-yl]-2-hydroxy-2-cyclohexyl-2-phenylcarboxylic ester To a solution of 3-azabicyclo[3.1.0]hexane-1-methylene-2-hydroxy-2-cyclohexyl-2-phenyl carboxylic acid ester (250 mg, 0.000760 mole), 5-bromo-2-methyl-2-pentene (148.6 mg, 0.000911 mole) in acetonitrile were added potassium carbonate (210.0 mg, 0.0015 mole) and potassium iodide (252 mg, 0.0015 mole). The reaction mixture was refluxed for 12 hours. After attaining room temperature, the reaction mixture was filtered and the filtrate was concentrated. The residue was taken in ethyl acetate and washed with water. The organic layer was dried over anhydrous Na$_2$SO$_4$ and concentrated under reduced pressure. The crude compound was purified by column chromatography (100-200 mesh, silicagel), eluting the compound with 15% ethyl acetate in hexane to give the desired product.

IR: 1722.9 cm$^{-1}$ $^1$HNMR (CDCl$_3$): 7.63-7.66 (m, 2H), 7.26-7.36 (m, 3M), 5.05-5.098 (bm, 1H), 4.24 (s, 2H), 3.71 (s, 1H), 2.95-3.02 (m, 2H), 2.26-2.37 (m, 2H), 2.19-2.24 (m, 2H), 1.79 (m, 2H), 0.75-1.32 (m, 19H), 0.512 (m, 1H).

Example 7

Preparation of (1α,5α)-[3-(3,4-methylenedioxyphenyl)ethyl]-3-azabicyclo[3.1.0]-hex-1-(methyl)-yl]-2-hydroxy-2-cyclohexyl-2-phenylcarboxylic ester (Compound No. 7)

To a solution of 3-azabicyclo[3.1.0]-hex-1-(methyl)-yl-2-hydroxy-2-cyclohexyl-2-phenyl carboxylic ester (250 mg, 0.0007 mole) and 3,4-methylenedioxyphenethyl bromide (207.8 mg, 0.00091 mole) in acetonitrile were added potassium carbonate (210 mg, 0.0051 mole) and potassium iodide (252.0 mg, 0.0051 mole). The reaction mixture was refluxed for 12 hours. After attaining room temperature, the reaction mixture was filtered, and the filtrate was concentrated. The residue was taken in ethyl acetate and washed with water, and brine. The organic layer was dried over anhydrous Na$_2$SO$_4$, filtered and concentrated under reduced pressure. The crude compound was purified by column chromatography (100-200 mesh, silicagel), eluting the compound with 15% ethylacetate in hexane to give the desired product.

IR: 1722.4 cm$^{-1}$ $^1$HNMR (CDCl$_3$): 7.66-7.64 (m, 2H), 7.24-7.37 (m, 3H), 6.60-6.74 (hi, 3H), 5.92 (s, 2H), 4.25 (s, 2H), 3.03 (bs, 1H), 2.97-3.03 (m, 2H), 2.53-2.59 (m, 4H), 2.20-2.26 (m, 2H), 1.04-1.32 (m, 13H), 0.52 (m, 1H).

Biological Activity

Radioligand Binding Assays:

The affinity of test compounds for M$_2$ and M$_3$ muscarinic receptor sub-types was determined by [$^3$H]-N-methylscopolamine binding studies using rat heart and submandibular gland respectively as described by Moriya et al., (*Life Sci*, 1999, 64(25):2351-2358) with minor modifications.

Membrane preparation: Submandibular glands and heart were isolated and placed in ice cold homogenising buffer (HEPES 20 mM, 10 mM EDTA, pH 7.4) immediately after sacrifice. The tissues were homogenised in 10 volumes of homogenising buffer and the homogenate was filtered through two layers of wet gauze and filtrate was centrifuged at 500 g for 10 min. The supernatant was subsequently centrifuged at 40,000 g for 20 min. The pellet thus obtained was resuspended in same volume of assay buffer (HEPES 20 mM, EDTA 5 mM, pH 7.4) and were stored at −70° C. until the time of assay.

Ligand binding assay The compounds were dissolved and diluted in DMSO. The membrane homogenates (150-250 µg protein) were incubated in 250 µl of assay buffer (HEPES 20 mM, pH 7.4) at 24-25° C. for 3 hours. Non-specific binding was determined in the presence of 1 µM atropine. The incubation was terminated by vacuum filtration over GF/B fiber filters (Wallac). The filters were then washed with ice cold 50 mM Tris HCl buffer (pH 7.4). The filter mats were dried and bound radioactivity retained on filters was counted. The IC$_{50}$ & Kd were estimated by using the non-linear curve fitting program using G Pad Prism software. The value of inhibition constant Ki was calculated from competitive binding studies by using Cheng & Prusoff equation (*Biochem Pharmacol*, 1973, 22: 3099-3108), Ki=IC$_{50}$/(1+L/Kd), where L is the concentration of [$^3$H]NMS used in the particular experiment. pKi=−(Log ki)

Functional Experiments Using Isolated Rat Bladder:

Methodology:

Animals were euthanized by overdose of urethane and whole bladder was isolated and removed rapidly and placed in ice cold Tyrode buffer with the following composition (mMol/L) NaCl 137; KCl 2.7; CaCl$_2$ 1.8; MgCl$_2$ 0.1; NaHCO$_3$ 11.9; NaH$_2$PO$_4$ 0.4; Glucose 5.55 and continuously gassed with 95% O$_2$ and 5% CO$_2$.

The bladder was cut into longitudinal strips (3 mm wide and 5-6 mm long) and mounted in 10 ml organ baths at 30° C., with one end connected to the base of the tissue holder and the other end connected to a polygraph through a force displacement transducer. Each tissue was maintained at a constant basal tension of 2 g and allowed to equilibrate for 1 hour during which the PSS was changed every 15 min. At the end of equilibration period, the stabilization of the tissue contractile response was assessed with 1 µmol/L of Carbachol consecutively for 2-3 times. Subsequently, a cumulative concentration response curve to carbachol (10$^{-9}$ mol/L to 3×10$^{-5}$ mol/L) was obtained. After several washes, once the baseline was achieved, cumulative concentration response curve was obtained in presence of NCE (NCE added 20 min. prior to the second CRC).

The contractile results were expressed as % of control E max. ED50 values were calculated by fitting a non-linear regression curve (Graph Pad Prism). pKB values were calculated by the formula pKB=−log [(molar concentration of antagonist/(dose ratio−1))]

where, dose ratio=ED50 in the presence of antagonist/ED50 in the absence of antagonist.

The results of the in-vitro testing tests are listed in Table II.

In-Vitro Test

TABLE II

| Compound No. | Receptor Binding Assay pKi | | Functional Assay pK$_B$ |
|---|---|---|---|
| | M$_2$ | M$_3$ | |
| 1 | 7.71 | 7.95 | 7.69 ± 0.15 |
| 2 | 8.2 | 8.54 | 7.74 ± 0.001 |
| 3 | 8.34 | 8.54 | 7.51 ± 0.33 |
| 4 | 4.8 | 5.1 | — |
| 5 | 6.75 | 6.96 | — |
| 6 | 9.16 | 8.74 | — |
| 7 | 8.96 | 8.62 | — |
| Tolterodine | 8.68 | 8.47 | 8.86 ± 0.12 |

While the present invention has been described in terms of its specific embodiments, certain modifications and equivalents will be apparent to those skilled in the art and are intended to be included within the scope of the present invention.

We claim:

1. Compounds defined by the structure of Formula I

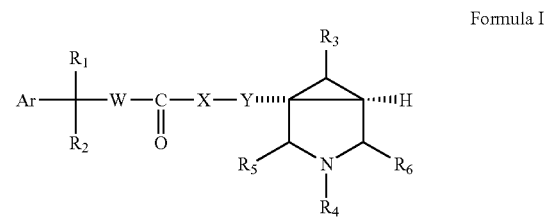

Formula I and their pharmaceutically acceptable salts, pharmaceutically acceptable, enantiomers, diastereomers, or N-oxides, wherein Ar represents phenyl;

R$_1$ represents a hydrogen, hydroxy, hydroxymethyl, amino, alkoxy, carbamoyl or halogen;

R$_2$ represents hydrogen, alkyl, C$_3$-C$_7$ cycloalkyl ring, a C$_3$-C$_7$ cycloalkenyl ring, or phenyl;

W represents (CH$_2$)$_p$, where p represents 0 to 1;

X represents an oxygen, sulfur, —NR or no atom, wherein R represents H or alkyl;

Y represents (CH$_2$)q wherein q represents 0 to 1;

R$_3$, R$_5$ and R$_6$ are independently selected from H, lower alkyl, COOH, CONH$_2$, NH$_2$, CH$_2$NH$_2$; and R$_4$ represents hydrogen, C$_1$-C$_{15}$ saturated or unsaturated aliphatic hydrocarbon (straight chain or branched) in which any 1 to 6 hydrogen atoms may be substituted with the group independently selected from halogen, arylalkyl, arylakenyl, heteroarylalkyl or heteroarylalkenyl, having 1-2 hetero atoms selected from the group consisting of nitrogen, oxygen and sulfur atoms with an option that any 1 to 3 hydrogen atoms on the ring in said arylalkyl, arylalkenyl, heteroarylalkyl, heteroarylalkenyl group may be substituted with lower alkyl ($C_1$-$C_4$), lower perhaloalkyl ($C_1$-$C_4$), cyano, hydroxy, nitro, lower alkoxycarbonyl, halogen, lower alkoxy ($C_1$-$C_4$), lower perhalo alkoxy ($C_1$-$C_4$), unsubstituted amino, N-lower alkylamino ($C_1$-$C_4$) or N-lower alkylamino carbonyl ($C_1$-$C_4$).

2. A compound selected from the group consisting of (1α,5α)-[3-benzyl-3-azabicyclo[3.1.0]-hex-1-(methyl)-yl]-2-hydroxy-2,2-diphenylcarboxylic ester (Compound No.1);

(1α,5α)-[3-benzyl -3-azabicyclo[3.1.0]-hex-1-(methyl)-yl]-2-hydroxy-2-cyclohex yl-2-phenylcarboxlic ester (Compound No.2);

(1α,5α)-[3-benzyl-3-azabicyclo[3.1.0]-hex-1-(methyl)-yl]-2-hydroxy-2-cyclopentyl-2-phenylcarboxylic ester (Compound No.3);

(1α,5α)-[3-benzyl-3-azabicyclo[3.1.0]-hex-1-yl]-2-hydroxymethyl-2-phenylacitamide (Compound No.4);

(1α,5α)-[3-benzyl-3-azabicyclo [3.1.0]-hex-1-yl]-2-hydroxy-2,2-diphenylacetamide (Compound No.5);

(1α,5α)-[3-(2-methyl-2-pentenyl)-3-azabicyclo[3.1.0]-hex-1-(methyl)-yl]-2-hydroxy-2-cyclohexyl-2-phenylcarboxylic ester (Compound No.6); and (1α,5α)-[3-(3,4-methylenedioxyphen)ethyl-3-azabicyclo [3.1.0]-hex-1-(methyl)-yl]-2-hydroxy-2-cyclohexyl-2-phenylcarboxylic ester (Compound No.7).

3. A pharmaceutical composition comprising a therapeutically effective amount of a compound as defined in claim 1 or 2 optionally together with pharmaceutically acceptable carriers, excipients or diluents.

* * * * *